United States Patent [19]
Farley et al.

[11] Patent Number: 5,397,314
[45] Date of Patent: Mar. 14, 1995

[54] SURGICAL CANNULA WITH BALL VALVE

[76] Inventors: Kevin Farley, 9 Via Salerno, Palm Coast, Fla. 32137; Daniel M. Gudeman, 526 Chesterfield La., Barrington, Ill. 60010

[21] Appl. No.: 149,538

[22] Filed: Nov. 9, 1993

Related U.S. Application Data

[63] Continuation-in-part of Ser. No. 959,221, Oct. 9, 1992.

[51] Int. Cl.$^6$ .................. A61M 5/00; F16K 15/00
[52] U.S. Cl. ................... 604/256; 604/167; 251/303; 137/527.6; 138/89
[58] Field of Search ............ 137/527, 527.6, 901; 251/303; 604/167, 169, 256, 905, 283, 246, 247; 138/89, 90, 46

[56] References Cited

U.S. PATENT DOCUMENTS

| | | |
|---|---|---|
| 60,082 | 11/1866 | Street et al. . |
| 265,310 | 10/1882 | Dyer .................. 137/527 |
| 1,034,995 | 8/1912 | Gannon . |
| 1,169,791 | 2/1916 | French ................ 251/303 |
| 2,989,283 | 6/1961 | Klingler .............. 251/303 |
| 4,036,210 | 7/1977 | Campbell et al. . |
| 4,112,932 | 9/1978 | Chiulli . |
| 4,201,241 | 5/1980 | Schertler ............. 137/527 |
| 4,233,982 | 11/1980 | Bauer et al. . |
| 4,240,411 | 12/1980 | Hosono . |
| 4,245,635 | 1/1981 | Kontos . |
| 4,261,357 | 4/1981 | Kontos . |
| 4,510,933 | 4/1985 | Wendt et al. . |
| 4,535,773 | 8/1985 | Yoon . |
| 4,601,710 | 7/1986 | Moll . |
| 4,617,929 | 10/1986 | Gill . |
| 4,794,911 | 1/1989 | Okada . |
| 4,796,615 | 1/1989 | Bullock et al. . |
| 4,917,668 | 4/1990 | Haindl . |
| 4,943,280 | 7/1990 | Lander . |
| 5,053,016 | 10/1991 | Lander . |
| 5,057,084 | 10/1991 | Ensminger et al. . |
| 5,098,394 | 3/1992 | Luther . |
| 5,104,383 | 4/1992 | Shichman . |
| 5,116,353 | 5/1992 | Green . |
| 5,125,915 | 6/1992 | Berry et al. . |
| 5,131,429 | 7/1992 | Nixon . |
| 5,141,498 | 8/1992 | Christian . |
| 5,180,373 | 1/1993 | Green et al. . |
| 5,180,376 | 1/1993 | Fischell . |
| 5,197,955 | 3/1993 | Stephens et al. . |
| 5,209,737 | 5/1993 | Ritchart et al. . |
| 5,226,879 | 7/1993 | Ensminger et al. . |
| 5,290,245 | 3/1994 | Dennis ................ 604/256 |

FOREIGN PATENT DOCUMENTS

| | | |
|---|---|---|
| 2267801 | 12/1975 | France . |
| 3048203 | 7/1982 | Germany . |
| 1078808 | 8/1967 | United Kingdom ......... 137/901 |

Primary Examiner—C. Fred Rosenbaum
Assistant Examiner—Mark Bockelman
Attorney, Agent, or Firm—Crossetta & Associates

[57] ABSTRACT

This invention relates to a surgical cannula that has a simple ball valve assembly comprising a ball, rotatably mounted on an axle extending between opposing legs of a pivotable yoke, which engages a seat to seal the instrument inlet to the cannula passageway when a trocar instrument is removed and moves out of the path of the instrument during insertion thus avoiding wear and strain on the valve and the instrumentation.

20 Claims, 5 Drawing Sheets

SURGICAL CANNULA WITH BALL VALVE

This application is a continuation-in-part of pending U.S. Ser. No. 959,221, filed Oct. 9, 1992, pending.

This invention relates to a surgical cannula and more particularly to a surgical cannula that utilizes a ball valve in a novel arrangement which significantly prolongs instrument life.

BACKGROUND OF THE INVENTION

Surgical cannulas are elongate hollow sleeves that are used to allow surgical instruments to be introduced through an animal body wall into a body cavity, preferably with minimal loss of body fluids and/or gases. Generally, in a first step of a surgical procedure a cannula is fitted with a stylet type trocar having a sharpened end and the assembly is pressed against the body such that the sharpened end of the stylet penetrates through the body wall. The cannula follows the sharpened end of the trocar through the opening with an exterior surface of the cannula sealing with the wall to resist loss of fluids. The sharpened stylet is generally removed and the interior channel of the cannula provides an entry passageway into the body cavity for the insertion of desired surgical instruments.

Often, when surgery is being performed using cannula means, a gas pressure is maintained in the targeted body cavity so that the body cavity is inflated to provide further room for surgical instruments to be conveniently manipulated within the body cavity. Thus, it is desirable that a cannula through which surgical instruments can be inserted into the body cavity, resists the passage of gases from the body cavity and/or is configured to allow the control of gaseous fluid to and/or from the body cavity.

It is known in the industry to use cannulas having trumpet valves incorporated therein. Trumpet valves generally clamp around the surgical instruments and must be manually manipulated during insertion and removal of the surgical instruments to maintain an adequate seal to prevent release of gas through the cannula. Trumpet valves can be difficult and cumbersome to manipulate and are generally seen by surgical personnel as inhibiting focused attention on the surgical procedure itself and as wearing or otherwise deteriorating costly insulated surgical trocar instruments.

It is also known in the industry to use cannulas having ball valves incorporated therein. Though ball valve assemblies are preferred by many in the industry to trumpet valve arrangements, the assemblies incorporating ball valve arrangements are generally seen as being difficult to sterilize for reuse, inconvenient for use with existing trocar instrumentation, cumbersome and generally also deteriorating to costly surgical trocar instrumentation.

It is an object of the present invention to provide an improved ball valve cannula arrangement which can be conveniently dissembled for sterilization and reuse.

It is another object of the invention to provide a ball valve cannula arrangement which can be operated in a way which does not significantly deteriorate surgical trocar instrumentation.

It is still a further object of the invention to provide a cannula ball valve arrangement which can be used with existing cannula.

It is still another object of the invention to provide a cannula ball valve arrangement having inexpensive disposable parts.

These and other objects of the invention will be apparent from the following recitation of the invention.

SUMMARY OF THE INVENTION

In accord with the present invention a novel ball valve assembly is provided for arrangement on an end portion of an elongated cannula which has a distal end configured for insertion into a body cavity.

As used herein, the cannula body comprises an elongated housing which defines an elongated cannula passageway running therethrough, the passageway being sized to accommodate through passage of surgical trocar instrumentation into a body cavity. The cannula body has a distal end that is arranged to have an opening from the cannula passageway interior of a body cavity and a proximal end which is arranged to have an opening from the cannula passageway exterior the body cavity. The ball valve assembly of the invention is arranged at the cannula body proximal end.

The ball valve assembly of the invention is preferably mounted in a hollow valve housing which generally defines a cavity having a generally oppositely disposed inlet and an outlet. The housing is arranged at the proximal end portion of the cannula body with the housing outlet being in fluid communication with the exterior opening of the cannula body. The cannula body generally also comprises a gas inlet/outlet. It should be understood that such may also be located in the valve housing of the invention.

The inlet, outlet and portion of the valve housing cavity therebetween, are sized to accommodate the insertion of surgical trocar instrumentation through the housing and into the cannula passage of the cannula body. Preferably, the inlet, outlet and cavity therebetween are collinearly arranged to allow passage of nonflexible trocar instrumentation therethrough into the cannula passageway. It should be understood that the valve housing can be integral with the cannula body or can be removably attached thereto.

The ball valve assembly of the invention comprises a ball, mounted on an axle extending between opposing legs of a yoke, and a seat, which are juxtaposed such that the ball and seat can engage and resist the flow of fluids through the inlet of the valve housing. The base of the yoke, which supports the opposing legs, is pivotally arranged so that the legs of the yoke, comprising the ball mounted therebetween, can pivot toward and away from the seat. The valve cavity is sized to allow pivoting of the ball sufficiently away from the seat to allow passage of trocar instrumentation inserted through the housing inlet, through the outlet and into the cannula body. Urging means are provided in an arrangement urging pivoting of the legs of the yoke to a normal first position wherein the ball engages the seat. The assembly further comprises urge override means, which is arranged to enable pivoting of the legs of the yoke toward a second position wherein the ball is disengaged from the seat.

In one embodiment of the invention, the ball valve assembly is detachable from the valve housing. In a preferred such embodiment, the valve assembly comprises a ball, seat, housing inlet, yoke, urging means and urge override means which are arranged on a detachable portion of the valve housing. In a specially preferred such embodiment, an end of the base of the yoke is pivotally mounted on an axle arranged on the detachable portion of the valve housing adjacent an opening to the housing inlet. Spring means is arranged to urge another end of the base such that a ball mounted between opposing legs of the yoke is urged to engage a seat in the passageway to the opening of the housing inlet. An urge override means, is arranged to engage the yoke and periodically urge the yoke to a position wherein the ball is away from the seat sufficient to allow unimpeded passage of non-flexible trocar instrumentation through the housing to the cannula body. Preferably, the urge override means comprises a rod or the like having an end arranged for axially engaging the yoke and another end which is arranged to extend through an opening in the detachable portion of the valve housing to be manually engaged by the operator.

In an especially preferred embodiment the end portion of the housing is threaded to engage mating threads of the valve housing for convenient attachment and detachment. In a still further preferred embodiment, trocar sealing means are arranged to engage an inserted trocar to resist the flow of fluids during the surgical procedure. Preferably, such sealing means is arranged at or about the inlet to the valve housing.

In another embodiment the valve housing is removably attached to the proximal end of the cannula body. In a preferred such embodiment the valve housing, or at least a portion thereof, is detachable from the cannula body and an end portion of the valve housing, comprising the valve assembly, is detachable from the detachable valve housing. In an especially preferred such arrangement, the valve housing comprising the outlet to the cannula body, is threaded to engage mating threads of the cannula body and is manufactured from a disposable material such as the various synthetic plastic materials or the like. The end portion comprising the valve assembly may be reusable or can also be manufactured from disposable materials and similarly so, the components of the valve assembly.

The ball may also be made of any suitable material but is preferably made of a lightweight material such as nylon or an elastomeric material. Mounting of the ball on the axle between opposing legs of the yoke can vary. In one embodiment the yoke, ball and seat may be precisely mounted and aligned such that the ball precisely engages the seat through a precise pivot. In another embodiment, the ball is loosely mounted to the axle so that it can freely rotate and will sealingly engage the seat at various positions in rotation when urged against the seat. Preferably also the ball is mounted capable of axial movement such that upon being urged against the seat the ball will find an appropriate optimum alignment with the seat. The seat is configured to generally accept a radius of the ball.

In operation, the distal end of the cannula body is inserted into a body cavity. When no instruments are disposed in the cannula, the urging means urges the ball, mounted between the opposing legs of the yoke, into a sealed position against the seat such that the entry or exit of fluids to and/or from the body cavity via the cannula is resisted. The pressure of fluid flow from the body cavity against the ball further enhances the sealing resistance to fluid flow from the cannula. Trocar instrumentation is inserted through the valve housing inlet, the urge override means is engaged and the ball is urged away from the seat to clear the passageway for unobstructed entry of the instrumentation. Sealing means, arranged at the valve inlet, engages the instrumentation and co-acting with the instrumentation seals the inlet from fluid flow. As the instrumentation travels past the ball the urge override means may be disengaged and the ball will rest atrumatically against the instrument rotating as the instrument passes through the valve housing outlet, into the cannula and into the body cavity. As the instrument is withdrawn the ball rotates and upon the instrument passing the ball, the urging means forces the ball against the seat to the inlet placing the valve in a sealed position. Thus, the trocar instrumentation can be safely removed from the cannula without significant fluid escape through the cannula.

DETAILED DESCRIPTION OF THE DRAWINGS

Figure 1:
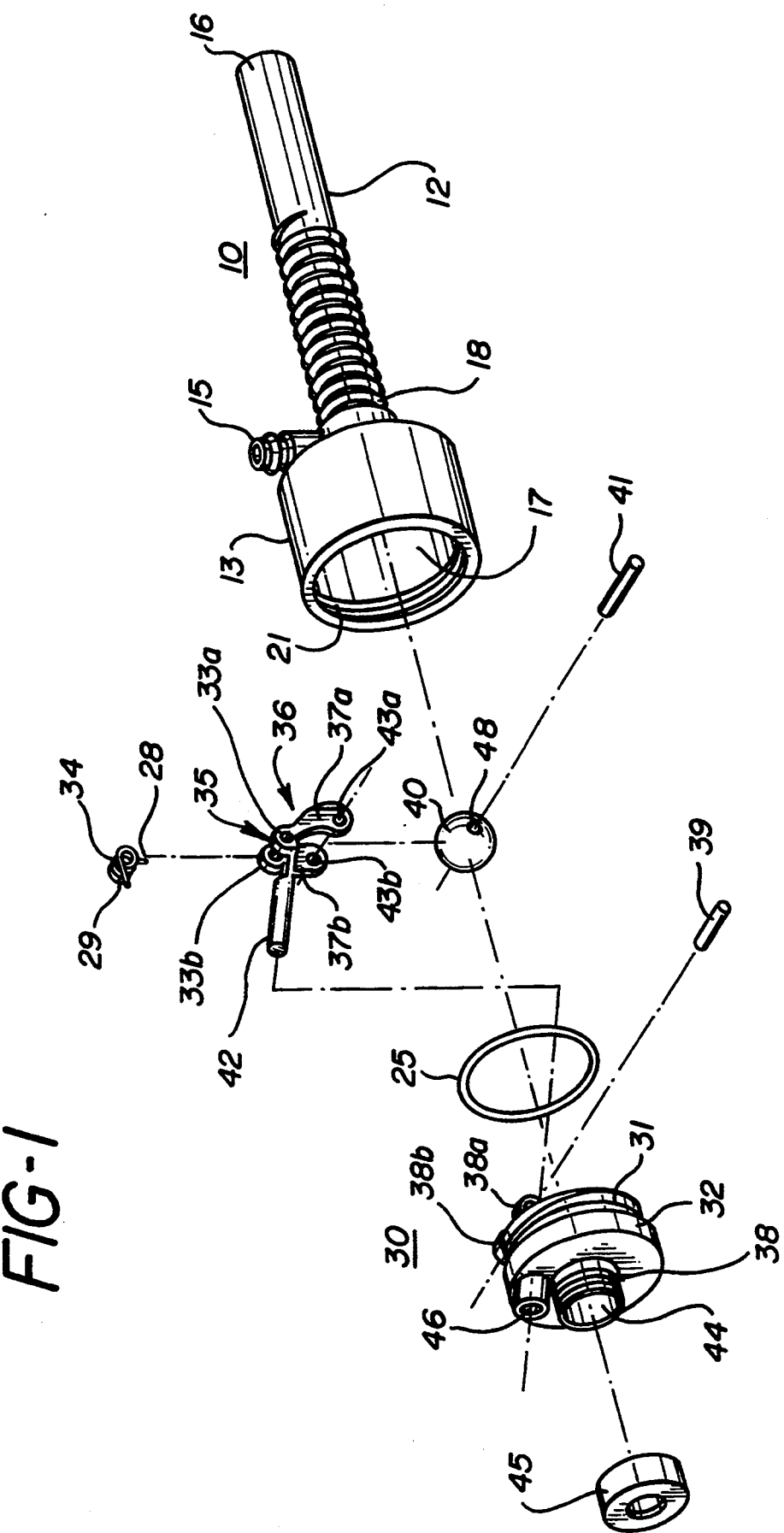
FIG. 1 is an exploded perspective illustration of an embodiment of a cannula of the invention.
Figure 2:
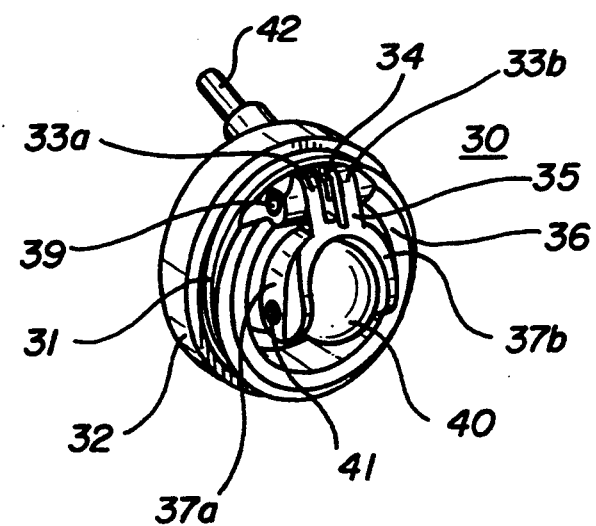
FIG. 2 is a perspective view of a ball valve assembly as illustrated in FIG. 1.
Figure 3:
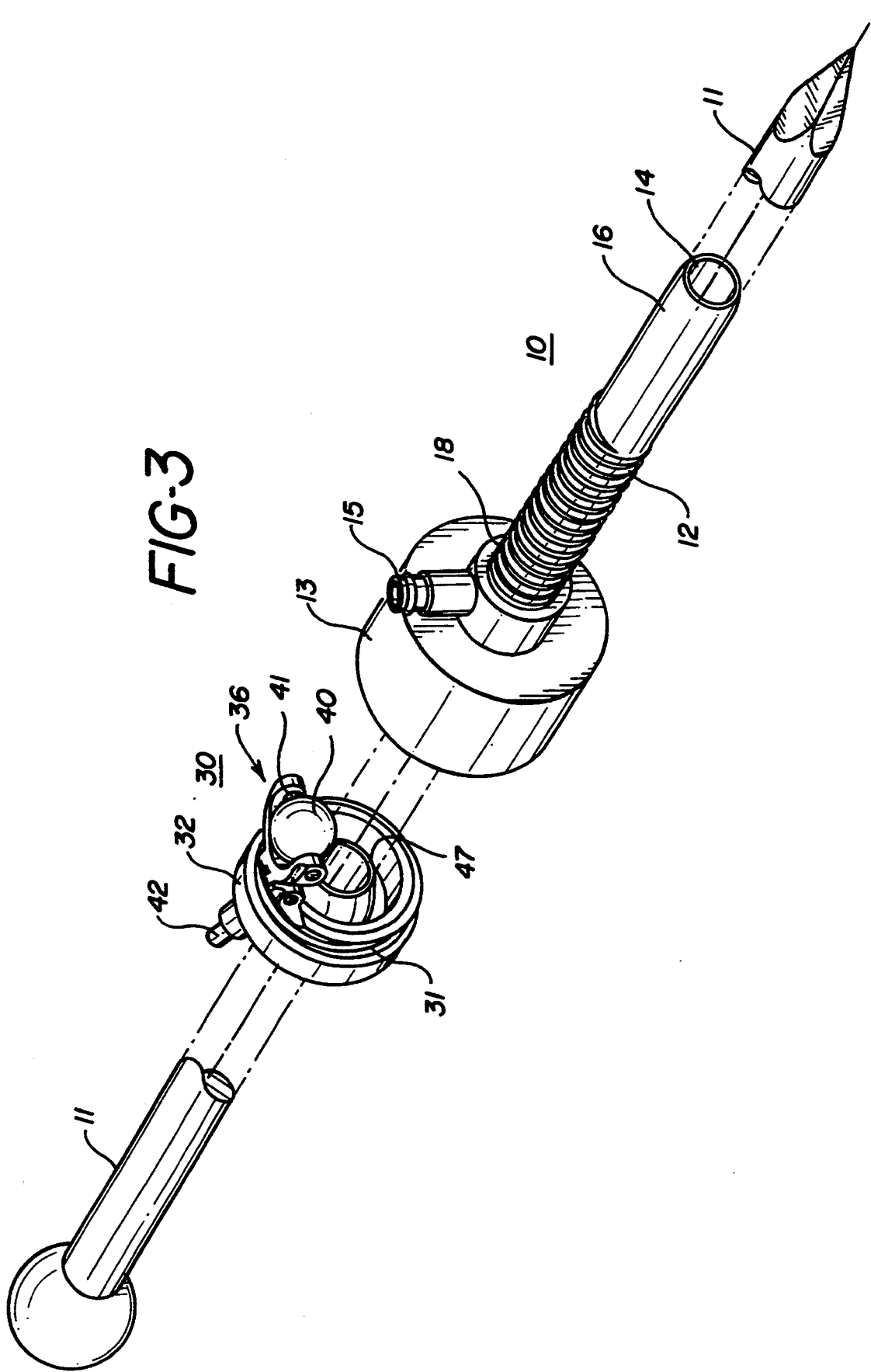
FIG. 3 is a partially exploded, sectional perspective illustration of a cannula of FIG. 1 containing a trocar instrument.

Referring first to FIGS. 1-3, therein is shown a cannula 10, comprising a hollow cannula body 12, defining a cannula passage 14 running therethrough. The cannula passage 14 is sized so as to accommodate surgical trocar instrumentation such as surgical stylet 11 disposed therethrough. The cannula body 12 comprises distal end 16, for insertion within a body cavity, proximal end 18, valve housing 13, gas inlet/outlet 15 and valve housing cavity 17.

Ball valve assembly 30 is illustrated as comprising valve housing end portion 32, spring 34, yoke 36, yoke base 35, yoke legs 37a and 37b, yoke base mounts 33a and 33b, ball 40, ball axle 41, urge override rod 42 and yoke base pivot axle 39. End portion 32 comprises inlet 44, inlet seal cap 45, urge override rod opening 46 and seat 47. Threads 31 of end portion 32 are arranged to mate with threads 21 of valve housing 13. Threads 38 of end portion 32 are arranged to mate with inlet seal cap 45. Sealing ring 25 is sized to fit over threads 31 and sealingly engage end portion 32 to valve housing 13.

In the embodiment of FIGS. 1-3, valve housing 13 is illustrated as being integral with cannula body 12 and the ball valve assembly being removably attached thereto. Pivot axle 39 is mounted through holes in housing yoke mounts 38a and 38b, which are in corresponding alignment with holes in yoke base mounts 33a and 33b and spring 34. Spring 34 is mounted in a loaded condition on pivot axle 39, with spring end 28 engaging yoke 36 and end 29 engaging end portion 32 in an arrangement urging yoke 36 to pivot toward seat 47. Ball axle 41 is mounted through aligned holes 43a and 43b in yoke legs 37a and 37b and through axial channel 48 of Ball 40. Inlet 44 of end portion 32 is sized to accommodate trocar instrumentation disposed therethrough and valve housing cavity 17 is additionally sized to accommodate such instrumentation with the ball valve assembly in an opened position.

In the operation of the device of FIGS. 1-3, the assembled apparatus is in a ready position with the ball urged against the seat by the interaction of the loaded spring against the yoke. A gas source is generally connected to the gas inlet/outlet of the cannula, the housing is generally grasped in one hand by the user, the urge override rod can be pushed forward toward the valve housing with a thumb or finger until the ball valve is urged to an open position. The first trocar instrument, usually a sharpened stylet 11 as illustrated in FIG. 3, is inserted through the inlet 44 into the cannula body and the urge override rod is released. The distal end of the cannula containing the sharpened stylet is pressed against the wall of the body cavity to be entered and with appropriate force the stylet pierces the body wall, the distal end of the cannula follows through the opening made by the stylet, with the body wall engaging the outer surface of the cannula to seal same from fluid loss. The stylet trocar is typically then removed by pulling back through the cannula wherein the urging action of the spring against the yoke forces the ball against the seat providing resistance from the reverse flow of gas through the housing inlet.

Figure 4:
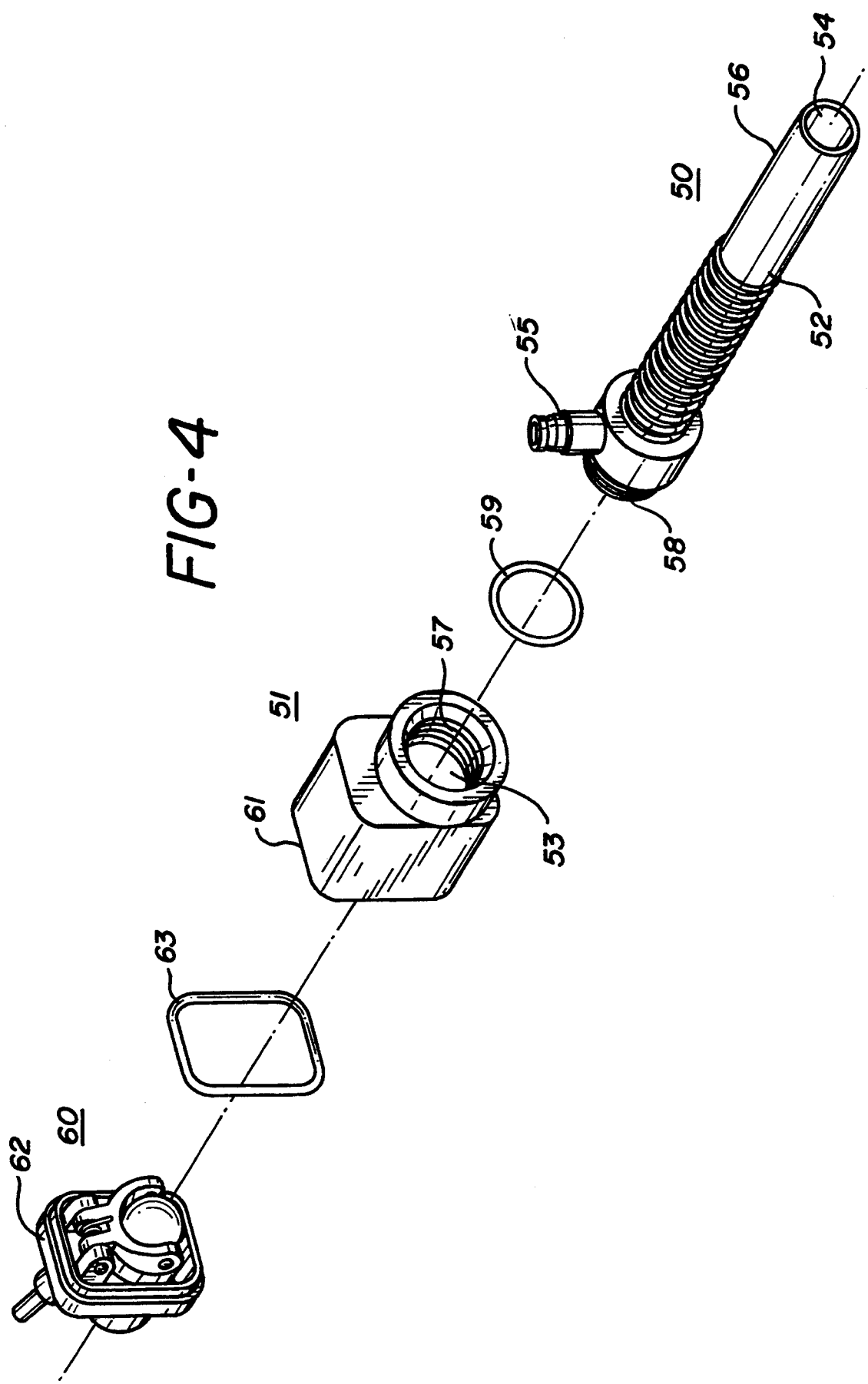
FIG. 4 is an exploded perspective view of another embodiment of a cannula of the invention.

FIG. 4, illustrates a further embodiment of the invention wherein the valve housing is removably attached to a cannula body which is particularly appropriate for applications wherein cleaning and sterilization may be problematic and the disposal of complex parts is desirable. Therein is shown a cannula 50, comprising a hollow cannula body 52, defining a cannula passage 54 running therethrough. The cannula passage 54 is sized so as to accommodate surgical trocar instrumentation disposed therethrough. The cannula body 52 comprises distal end 56, for insertion within a body cavity, threaded proximal end 58 and gas inlet/outlet 55. Valve housing 51 comprises outlet 53 having threads 57 which mate with threads at proximal end 58 of the cannula body. Sealing ring 59 is sized to seal the threaded joining of valve housing and cannula distal end. Ball valve assembly 60 comprises valve housing end portion 62 which is configured to sealingly engage end 61 of the valve housing, with seal 63 being sized to assure adequate seal. The component parts of the ball valve assembly are as illustrated in FIGS. 1-3. In this embodiment the valve assembly is illustrated as being joined by glue, press fit or the like to the valve housing with both the valve assembly and valve body being disposable.

Figure 5:
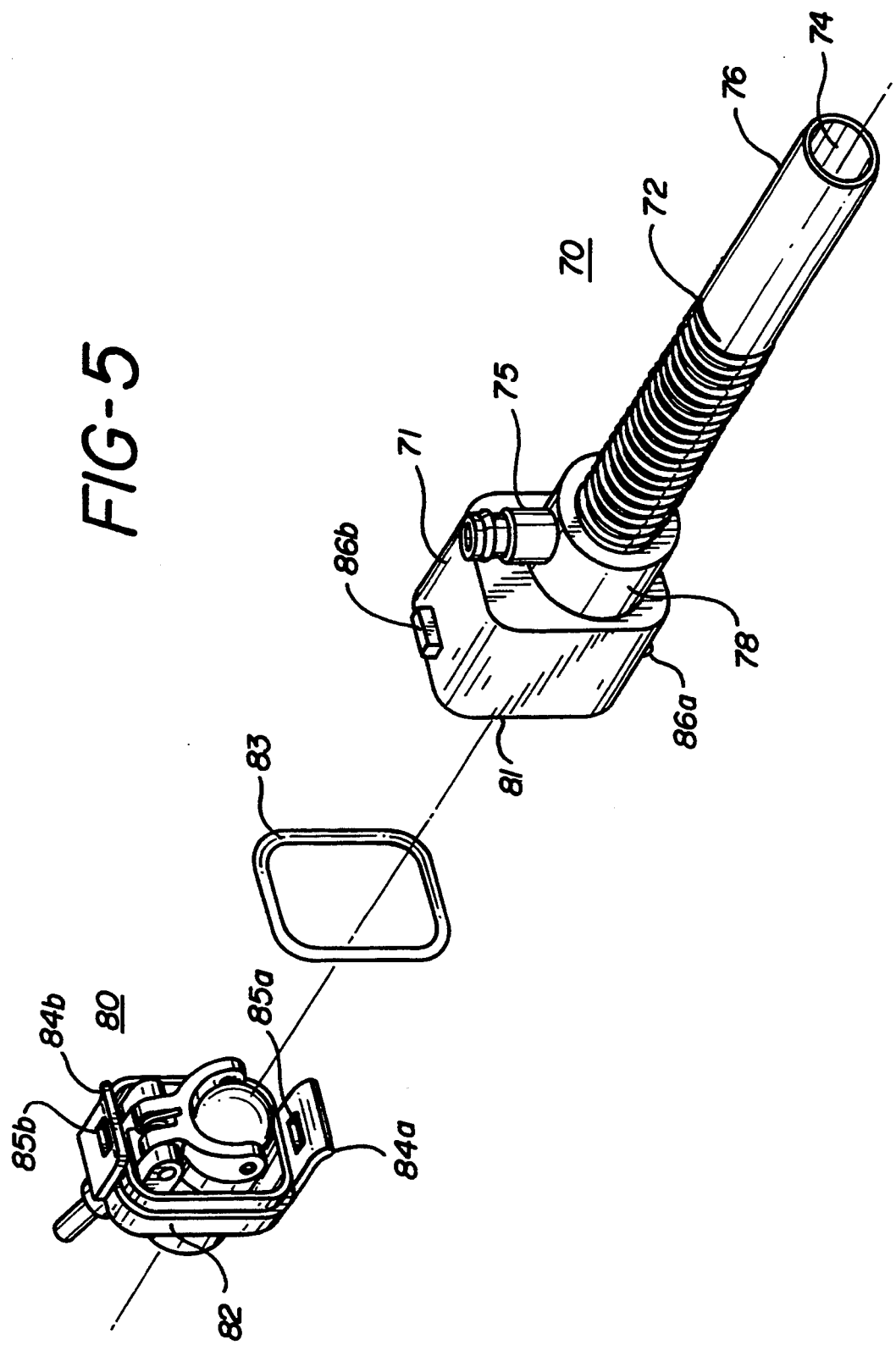
FIG. 5 is an exploded perspective view of still another embodiment of a cannula of the invention.

FIG. 5, illustrates a further embodiment of the invention wherein the valve housing is removably attached to a cannula body and the ball valve assembly is removably attached from the valve housing. This embodiment is particularly appropriate for applications wherein various sized ball valve arrangements are desired and cleaning and sterilization problems dictate the disposal of only select parts. Therein is shown a cannula 70, comprising a hollow cannula body 72, defining a cannula passage 74 running therethrough. The cannula passage 74 is sized so as to accommodate surgical trocar instrumentation disposed therethrough. The cannula body 72 comprises distal end 76, for insertion within a body cavity, proximal end 78 and gas inlet/outlet 75. Valve housing 71 is illustrated as integral with the cannula body. Ball valve assembly 80 comprises valve housing end portion 82 which is configured to sealingly engage end 81 of the valve housing, with seal 83 being sized to assure adequate seal. Snap clips 84a and 84b are provided on end portion 82 with openings 85a and 85b sized to enable locking engagement with lock studs 86a and 86b of the valve housing. The component parts of the ball valve assembly are as illustrated in FIGS. 1-3. In this embodiment the valve assembly is illustrated as being a modular unit which can be snap locked on or off the valve housing with minimum effort.

It should be understood that it is contemplated that the arrangement of the valve housing with the cannula body can vary widely and not depart from the scope of the invention. Thus, the valve housing can be of significantly different shape than illustrated and can be formed of any suitable materials or combination of materials. Further, although the movable ball is preferably made of nylon, the ball can be made of any suitable material and may also be fabricated of a material that exhibits a certain amount of deformation such that the ball may conform somewhat to the seat to better seal the valve.

Valve assemblies and/or valve housings may have different sized openings which allows for a cannula that can accommodate various sized instruments while using the same valve and achieving a seal with different sized instruments. While certain present preferred embodiments have been shown and described, it should be understood that the invention is not limited thereto and various modifications of the invention are evident which can be seen as providing equivalent functions, each of which are contemplated as within the scope of the invention.

We claim:

1. In a surgical cannula, having a hollow body defining a cannula passageway sized to receive instruments running therethrough, a distal end configured for insertion into a body cavity and a proximal end having an opening to said cannula passageway, the improvement comprising:
   a ball valve assembly, arranged at said proximal end of said cannula proximate said opening to said cannula passageway, said assembly comprising a ball, rotatably mounted on an axle extending between opposing legs of a yoke, and a seat;
   said seat being configured to receive said ball and comprising an opening, which is aligned in a path with said opening to said cannula passageway and is sized to receive instruments running therethrough;
   means for pivoting said yoke from a first position, wherein said ball engages said seat within said path between said opening of said seat and said opening to said cannula passageway, to another position;
   means for urging said yoke, about said pivot, to said first position;
   means for urging said yoke, about said pivot, from said first position to said another position.

2. The cannula of claim 1 comprising a valve housing, arranged at said proximal end of said cannula and comprising an outlet at a first end, in fluid communication with said opening to said cannula passageway, an inlet at a second end and a cavity arranged therebetween sized to accept said ball valve assembly.

3. The cannula of claim 2 wherein said yoke is pivotally mounted to said second end and said opening of said seat is in fluid communication with said inlet at said second end.

4. The cannula of claim 3 wherein said means for urging said yoke from said first position to said another position comprises a push rod, which extends through an opening in said second end.

5. The cannula of claim 3 wherein said yoke is pivotally mounted to an axle and spring means is arranged to urge said yoke about said axle to said first position.

6. The cannula of claim 2 wherein said valve housing is removably connected to said proximal end of said cannula body.

7. The cannula of claim 6 wherein said second end is removably connected to said valve housing.

8. The cannula of claim 2 wherein said valve housing is integral with said proximal end of said cannula body.

9. The cannula of claim 2 wherein said second end is removably connected to said valve housing.

10. The cannula of claim 1 wherein said means for urging said yoke to said first position comprises spring means.

11. The cannula of claim 1 wherein said means for urging said yoke from said first position to said another position comprises a push rod.

12. The cannula of claim 1 wherein said ball is loosely mounted on said axle extending between opposing legs of said yoke.

13. The cannula of claim 1 wherein said opening to said cannula passageway and said opening of said seat are collinear.

14. The cannula of claim 1 comprising sealing means, arranged so that said opening of said seat is sealed upon insertion of an instrument therethrough.

15. A surgical cannula comprising:
- a hollow body, defining a cannula passageway sized to receive instruments running therethrough, having a distal end configured for insertion into a body cavity and a proximal end comprising an opening to said cannula passageway;
- a valve housing, arranged at said proximal end of said cannula and comprising an outlet at a first end, in fluid communication with said opening to said cannula passageway, an inlet at a second end and a cavity arranged therebetween;
- a ball valve assembly, arranged at said second end of said valve housing, said assembly comprising a ball, rotatably mounted on an axle extending between opposing legs of a yoke, and a seat;
- said seat being configured to receive said ball and comprising an opening to said inlet, said opening to said inlet being aligned in a path with said opening to said cannula passageway and being sized to receive instruments running therethrough;
- means for pivoting said yoke from a first position, wherein said ball engages said seat within said path between said opening of said seat and said opening to said cannula passageway, to another position;
- means for urging said yoke, about said pivot, to said first position;
- means for urging said yoke, about said pivot, from said first position to said another position;
- wherein said means for urging said yoke from said first position to said second position is actuatable exterior said housing.

16. The cannula of claim 15 wherein said valve housing is removably connected to said proximal end of said cannula body.

17. The cannula of claim 15 wherein said second end is removably connected to said valve housing.

18. The cannula of claim 15 wherein said yoke is pivotally mounted to an axle and spring means is arranged to urge said yoke about said axle to said first position.

19. The cannula of claim 15 wherein said means for urging said yoke from said first position to said another position comprises a push rod.

20. A ball valve assembly for use with a surgical cannula comprising:
- a valve housing, attachable to a proximal end of said cannula and comprising an outlet at a first end, in fluid communication with an opening to a passageway in said cannula sized for the insertion of instruments therethrough, an inlet at a second end and a cavity therebetween;
- a ball valve, arranged in said cavity at said second end of said valve housing, said ball valve comprising a ball, rotatably mounted on an axle extending between opposing legs of a yoke, and a seat comprising an opening to said inlet;
- said seat being configured to receive said ball, said opening to said inlet being aligned in a path with said opening to said cannula passageway, and being sized to receive instruments running therethrough;
- means for pivoting said yoke from a first position, wherein said ball engages said seat within said path between said opening of said seat and said opening to said cannula passageway, to another position;
- means for urging said yoke, about said pivot, to said first position;
- means for urging said yoke, about said pivot, from said first position to said another position.

* * * * *